United States Patent [19]

Davidson

[11] 4,050,457
[45] Sept. 27, 1977

[54] SANITARY MOUTH-TO-MOUTH SHIELD

[76] Inventor: Stacy D. Davidson, 3240 Aden St., Memphis, Tenn. 38127

[21] Appl. No.: 508,247

[22] Filed: Sept. 23, 1974

[51] Int. Cl.$^2$ .............................................. A61M 16/00
[52] U.S. Cl. .............................. 128/145.5; 128/132 R
[58] Field of Search ............... 128/132 R, 132 D, 136, 128/139, 140, 145.5, 146.2, 208, 351, DIG. 26

[56] References Cited

U.S. PATENT DOCUMENTS

| | | | |
|---|---|---|---|
| 1,270,565 | 6/1918 | Teter | 128/208 |
| 3,049,121 | 8/1962 | Brumfield et al. | 128/146.2 |
| 3,137,293 | 6/1964 | Green | 128/145.5 |
| 3,286,713 | 11/1966 | Kurtz et al. | 128/156 |
| 3,626,936 | 12/1971 | Barker | 128/145.5 |
| 3,802,428 | 4/1974 | Sherman | 128/145.5 |
| 3,834,384 | 9/1974 | Raines | 128/146.2 |

Primary Examiner—Dalton L. Truluck
Attorney, Agent, or Firm—John R. Walker, III

[57] ABSTRACT

A shield for use in mouth-to-mouth or mouth-to-nose resuscitation. The shield is constructed of a one piece sheet of thin flexible material capable of assuming complimentary sealing relationship over a patient's face and includes dimensions sufficient to cover the face from ear-to-ear and from the bridge of the nose to the bottom of the chin. The shield includes a mouth opening located substantially centrally thereof and adapted to fit over a patient's mouth to permit air to be blown therethrough into the patient's lungs in mouth-to-mouth resuscitation. A lip flap can be optionally provided around the periphery of the mouth opening and a second opening can be provided in spaced relationship with the mouth opening for use in mouth-to-nose resuscitation.

5 Claims, 4 Drawing Figures

SANITARY MOUTH-TO-MOUTH SHIELD

BACKGROUND OF THE INVENTION

This invention relates to the art of artificial respiration, and is more particularly concerned with mouth-to-mouth or mouth- to-nose resuscitation.

It is now recognized that, in many rescue attempts, manual methods of manipulating the victim's body to restore oxygen to the victim are inadequate to ventilate the victim's lungs to the extent necessary to effect a recovery. Consequently, it is now widely preferred that the power and substantial capacity of the rescuer's lungs be utilized to rapidly deliver large volumes of air under sufficient pressure to adequate lung inflation of the victim, and hence there is more and more admonition to use the mouth-to-mouth method. In such method it is only necessary to place the victim on his back, open his mouth to check airway obstruction, draw chin forward with thumb, pinch off nostrils, extend (straighten) the neck, tilt the head backward, press on forehead, make air tight seal with lips around mouth opening, and proceed immediately to evenly blow a deep breath into him. In the case of drowning, particularly, the victim's very immediate need is oxygen, and since the time required to supply the oxygen is at an absolute minimum when mouth-to-mouth resuscitation is administered, dramatic rescues have been effected by this method.

Notwithstanding the widely recognized advantages of mouth-to-mouth resuscitation, many would-be rescuers are understandably reluctant to employ the method because of the intimate personal contact required and the ofttimes repulsive condition or appearance of the victim.

In certain rescue operations, the victim is injured in the mouth or closely adjacent areas, such as severe cuts, which prevents mouth-to-mouth resuscitation and leaves mouth-to-nose resuscitation as an alternate possibility. However, mouth-to-nose resuscitation requires the same personal contact which makes the rescuer reluctant to participate.

A number of prior art devices have been invented for use in mouth-to-mouth resuscitation. However, the art devices use a number of rigid or semi-rigid structures which do not provide an effective seal to insure that the air is blown into the victim's lungs, thus, allowing some of the air to escape around the victim's lips and reduce the effectiveness of the method.

SUMMARY OF THE INVENTION

The device of the present invention comprises a shield for use in mouth-to-mouth or mouth-to-nose resuscitation. The shield is constructed of a one piece sheet of thin flexible material capable of assuming complimentary sealing relationship over a patient's face and includes dimensions sufficient to cover the face from ear-to-ear and from the bridge of the nose to the bottom of the chin. The shield includes a mouth opening located substantially centrally thereof and adapted to fit over a patient's mouth to permit air to be blown therethrough into the patient's lungs in mouth-to-mouth resuscitation. A lip flap can be optionally provided around the periphery of the mouth opening and a second opening can be provided in spaced relationship with the mouth opening for use in mouth-to-nose resuscitation.

It is, therefore, a primary object of the present invention to provide a simple, small, and inexpensive shield for use by the rescuer in mouth-to-mouth resuscitation which avoids the necessity for personal contact with the victim and thus removes any hesitancy the rescuer may have to use the vital direct resuscitation method without sacrificing the effectiveness of the method.

The above and other objects and advantages of the invention will become apparent upon consideration of the following specification and the accompanying drawing wherein there is disclosed a preferred embodiment of the invention.

DESCRIPTION OF THE PREFERRED EMBODIMENT

Figure 1:
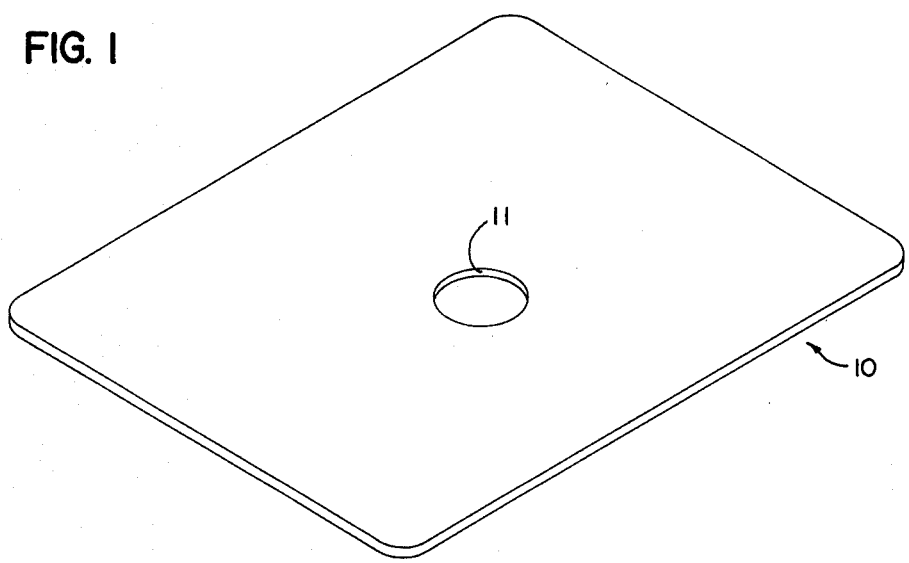
FIG. 1 is a perspective view of a shield constructed in accordance with the principles of the present invention.
Figure 2:
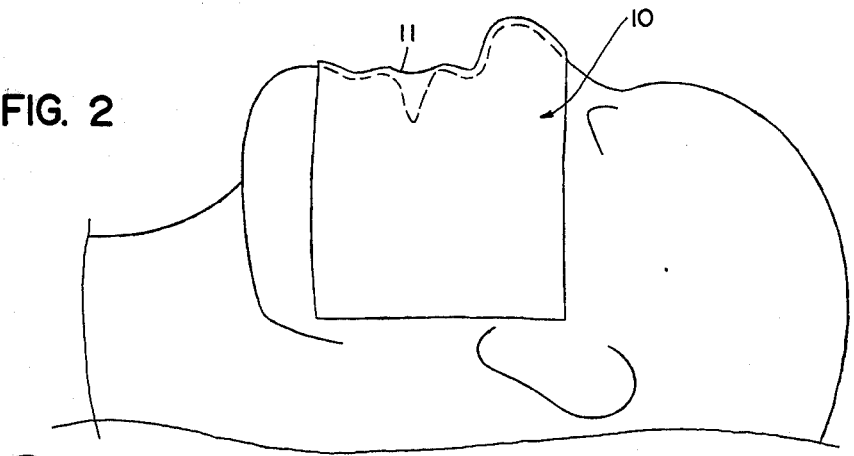
FIG. 2 is a side elevation of shield of FIG. 1, shown in position on a victim's mouth.
Figure 3:
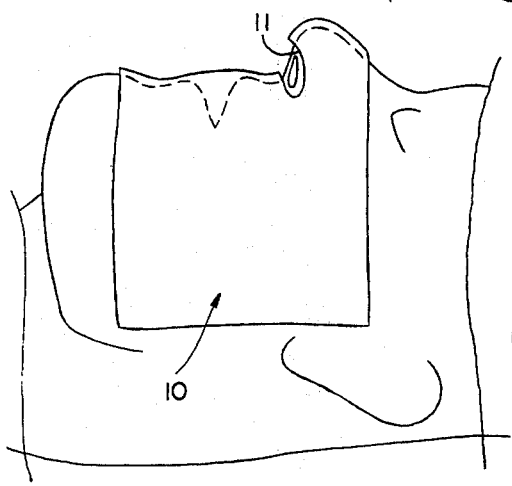
FIG. 3 is a side elevation of the shield of FIG. 1, shown in position on a victim's nose.
Figure 4:
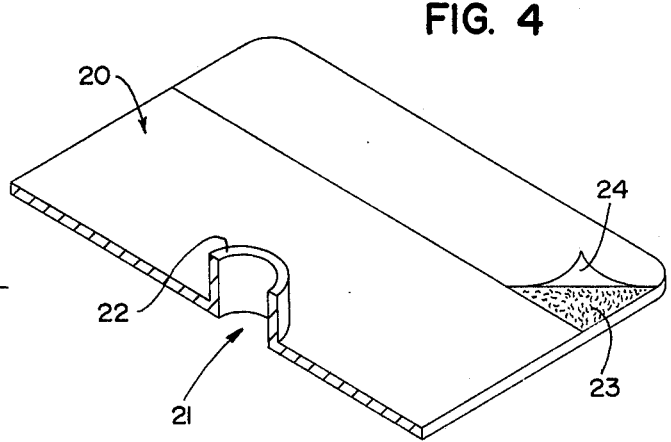
FIG. 4 is a fragmentary perspective view showing a modification of the shield shown in FIGS. 1-3.

Referring to the drawings, one embodiment of the mouth-to-mouth shield is shown in FIG. 1 and generally represented by reference number 10 and a second embodiment is shown in FIG. 4 which is generally represented by the reference numeral 20.

The shield 10, shown in FIG. 1, is constructed in the form of a thin, flat flexible sheet of material, such as plastic, rubber, rubberized cloth or other suitable material which will allow the sheet of material to readily conform to the contours of a victim's face in the mouth and nose area and which can be easily folded for packaging. The shield 10 is substantially rectangular in configuration and is constructed to include dimensions sufficient to allow the shield to extend from ear-to-ear and to extend from the bridge of the nose to the base of the chin. To accomodate various age victims, the shield can be constructed in a number of sizes, such as small, medium or large. A mouth opening 11 is provided in substantially a central location on shield 10 and is detailed to permit oxygen to be blown freely into the victim's lungs in mouth-to-mouth resuscitation. In use of shield 10, the material will conform to the curvature of the victim's face and will provide an effective shield over the lips to permit mouth-to-mouth resuscitation without intimate contact between the rescuer and the victim and at the same time permits an effective seal to prevent escape of air around the victim's lips.

FIG. 4 shows a modified shield including a lip flap construction 22 which extends around the periphery of the mouth opening 21 to permit the mouth to be more easily located relative to opening 21 and to provide additional shield means between the rescuer and the victim. A similar lip flap can be provided around the mouth opening 11 of shield 10. Shield 20 is also provided with an adhesive coating 23 on the underside and adjacent opposite ends of the shield for use in holding the shield in place on a victim's face. A removable cover tab 24 is provided over the adhesive coating 23 to prevent unwanted sticking before use. Tab 24 is removed and the adhesive coating 23 is stuck to the side of the victim's head during use.

Both of the shields 10, 20 can be produced for permanent use by sanitizing after use, or can be produced as disposable items in sterile packages which are discarded after use.

The sanitary shields 10, 20 are used by placing the shields over a victim's face so that the mouth openings 11, 21 are aligned with the victim's mouth and with the sheet material effectively covering the victim's lips to prevent intimate contact between the rescuer and the victim. Should the shield include lip flaps, the flap is inserted into the victim's mouth.

After the shield is effectively positioned, mouth-to-mouth resuscitation is carried out by following the required mouth-to-mouth resuscitation procedures.

Shield 10 can also be used to perform mouth-to-nose resuscitation, if the victim's mouth is severly injured, by correctly positioning the opening 11 over the victim's nose entrance and following the normal mouth-to-mouth procedures. Shield 10 will allow effective mouth-to-nose resuscitation and still prevent intimate contact between rescuer and victim.

Shield 20 could be used in mouth-to-nose resuscitation by positioning shield 20 with mouth opening 21 over the victim's nostrils with lip flaps 22 turned out. The thin sheet of material is flexible enough to make a seal with the mouth around the nose and still prevent intimate contact. Also, the shields 10, 20 could be used in performing mouth-to-trachea resuscitation.

Although the invention has been described and illustrated with respect to preferred embodiments thereof, it is not to be so limited since changes and modifications may be made therein which are within the full intended scope of the invention.

I claim:

1. A device for use in mouth-to-mouth, mouth-to-trachea or mouth-to-nose resuscitation comprising a one piece sheet of thin flexible material capable of assuming complementary sealing relationship over the contour of a person's face and of sufficient dimensions to cover the face in the mouth and nose area and including an unobstructed opening located substantially centrally of said sheet and sized to be operably positioned over a patient's mouth, trachea or nose whereby an effective seal can be made between said patient's mouth, trachea or nose and a rescuer's mouth through the portion of said sheet surrounding said opening when said rescuer presses his mouth against said patient's mouth, trachea or nose through said sheet to prevent air escape around said patient's mouth, trachea or nose and to permit air to be blown therethrough into said patient's lungs in mouth-to-mouth, mouth-to-trachea, or mouth-to-nose resuscitation.

2. A device as defined in claim 1 further characterized in that said shield includes a lip flap extending around the periphery of said mouth opening.

3. A device as defined in claim 1 further characterized in that said shield is constructed of dimensions sufficient to extend from ear-to-ear and from the bridge of the nose to the chin.

4. A device as defined in claim 1 further characterized in that said shield includes adhesive coating means adjacent to the opposite end thereof for use in holding the shield in place on a victim.

5. A device as defined in claim 1 further characterized in that said includes removable cover tabs over said adhesive coating means.

* * * * *